(12) United States Patent
Holmes-Farley

(10) Patent No.: US 7,049,345 B2
(45) Date of Patent: May 23, 2006

(54) FAT-BINDING POLYMERS

(75) Inventor: Stephen Randall Holmes-Farley, Arlington, MA (US)

(73) Assignee: Genzyme Corporation, Cambridge, MA (US)

( * ) Notice: Subject to any disclaimer, the term of this patent is extended or adjusted under 35 U.S.C. 154(b) by 405 days.

(21) Appl. No.: 10/187,315

(22) Filed: Jun. 27, 2002

(65) Prior Publication Data

US 2003/0039626 A1    Feb. 27, 2003

Related U.S. Application Data

(60) Provisional application No. 60/302,081, filed on Jun. 29, 2001, provisional application No. 60/302,221, filed on Jun. 29, 2001, provisional application No. 60/359,473, filed on Feb. 22, 2002, provisional application No. 60/359,467, filed on Feb. 22, 2002, provisional application No. 60/359,474, filed on Feb. 22, 2002.

(51) Int. Cl.
*A61K 47/30* (2006.01)

(52) U.S. Cl. .................. 514/772.33; 424/400
(58) Field of Classification Search ............... 424/400; 514/772.33
See application file for complete search history.

(56) References Cited

U.S. PATENT DOCUMENTS

| | | | |
|---|---|---|---|
| 3,780,171 A | 12/1973 | Irmscher et al. | |
| 3,923,972 A | 12/1975 | Fields et al. | |
| 4,160,826 A | 7/1979 | Fischetti | |
| 4,211,765 A | 7/1980 | Johnson et al. | |
| 4,218,443 A | 8/1980 | Comai et al. | |
| 4,265,879 A | 5/1981 | Fields et al. | |
| 4,302,450 A | 11/1981 | Comai et al. | |
| 4,432,968 A | 2/1984 | Page et al. | |
| 4,598,089 A | 7/1986 | Hadvary et al. | |
| 4,959,179 A | 9/1990 | Aronson et al. | |
| 5,063,210 A | 11/1991 | Lange, III et al. | |
| 5,089,163 A | 2/1992 | Aronson et al. | |
| 5,137,716 A | 8/1992 | Weisenfeld | |
| 5,200,183 A | 4/1993 | Tang et al. | |
| 5,286,481 A | 2/1994 | Weisenfeld | |
| 5,308,766 A | 5/1994 | Dennis et al. | |
| 5,376,674 A | 12/1994 | Derungs et al. | |
| 5,401,498 A | 3/1995 | Kesseler et al. | |
| 5,427,919 A | 6/1995 | Dennis et al. | |
| 5,453,282 A | 9/1995 | Kanauchi et al. | |
| 5,453,429 A | 9/1995 | Bliem et al. | |
| 5,474,993 A | 12/1995 | Rubin et al. | |
| 5,484,777 A | 1/1996 | Lange, III et al. | |
| 5,567,597 A | 10/1996 | Dennis et al. | |
| 5,569,452 A | 10/1996 | Amidon et al. | |
| 5,597,810 A | 1/1997 | Hoffman et al. | |
| 5,607,669 A | 3/1997 | Mandeville, III et al. | |
| 5,618,530 A | 4/1997 | Mandeville, III et al. | |
| 5,624,963 A | 4/1997 | Mandeville, III et al. | |
| 5,665,348 A | 9/1997 | Okayama et al. | |
| 5,679,717 A | 10/1997 | Mandeville, III et al. | |
| 5,693,675 A | 12/1997 | Mandeville, III et al. | |
| 5,703,188 A | 12/1997 | Mandeville, III et al. | |
| 5,750,524 A | 5/1998 | Mera et al. | |
| 5,900,233 A | 5/1999 | Day | |
| 5,900,475 A | 5/1999 | Mandeville, III et al. | |
| 6,030,953 A | 2/2000 | Bailly et al. | |
| 6,264,937 B1 | 7/2001 | Mandeville, III et al. | |
| 6,299,868 B1 | 10/2001 | Jozefiak et al. | |
| 6,358,522 B1 | 3/2002 | Hug et al. | |
| 6,726,906 B1 * | 4/2004 | Jozefiak et al. ......... | 424/78.35 |

FOREIGN PATENT DOCUMENTS

| | | |
|---|---|---|
| EP | 0 050 347 | 4/1982 |
| EP | 0 129 748 | 1/1985 |
| EP | 0 381 262 | 8/1990 |
| EP | 0 050 346 | 4/1994 |
| FR | 2 081 400 | 12/1971 |
| JP | 04333694 | 11/1992 |
| JP | 06 321787 | 11/1994 |
| WO | WO 89/07455 | 8/1989 |
| WO | WO 01/05408 A1 | 1/2001 |

OTHER PUBLICATIONS

Gargouri, Y. et al., "Ajoene prevents fat digestion by human gastric lipase in vitro," *Biochimica et Biophysica Acta.* 1006:137-139 (1989).

Gargouri, Y et al., "Covalent inhibition of digestive lipases: an in vitro study," *Biochimica et Biophysica Acta.* 1344:6-37 (1997).

Karamac, M. and Amarowicz, R., "Inhibition of Pancreatic Lipase by Phenolic Acids, Examination in vitro," *Verlag der Zeitschrift für Naturforschung*:903-905 (1996).

Marguet, F., et al., "Digestive lipases: inactivation by phosphonates," *Biochimica et Biophysica Acta.* 1210:157-166 (1994).

Mannesse, M.L.M., et al., "Phosphonate analogues of triacylglycerols are potent inhibitors of lipase," *Biochimica et Biophysica Acta.* 1259:56-64 (1995).

Martichonok, V. and Jones, J.B., "(Z) -Heptadec-8-enylboronic acid: a potential lipase inhibitor," *J. Chem. Soc. Perkin Trans.* I:2927-2929 (1995).

(Continued)

*Primary Examiner*—Gollamudi S. Kishore
*Assistant Examiner*—Eric E. Silverman
(74) *Attorney, Agent, or Firm*—Fish & Neave IP Group Ropes & Gray, LLP

(57) ABSTRACT

The present invention provides fat-binding polymers, which comprise dialkanolamine, dialkanolammonium, aminoalkylpolyol, and ammoniumalkylpolyol pendant groups for subjects in need of fat removal from the gastrointestinal tract, particularly subjects suffering from steatorrhea and/or experiencing side effects from lipase inhibitors. Patients being administered with lipase inhibitors are typically being treated for Type II Diabetes, streatorrhea, and hypertriglyceridemia. The fat binding polymers of this invention are also suitable for use with obese subjects.

42 Claims, No Drawings

OTHER PUBLICATIONS

Vainio, P., et al., "Inhibition of Lipoprotein Lipase by Benzene Boronic Acid Effect of Apolipoprotein C-II," *Biochimica et Biophysica Acta*. 711:386-390 (1982).

Bagree, A., et al., "Modification of Epsilon-Amino Group of Lysine in Proteins by Acylation with Pyromellitic Dianhydride and O-Sulphobenzoic Anhydride," *FEBS Letters* 120(2):275-277 (1980).

Stadler, P., et al., "Inhibition of microbial lipases with stereoisomeric triradylglycerol analog phosphonates," *Biochimica et Biophysica Acta*. 1304:229-244 (1996).

Kawaguchi, K., et al., "Hesperidin as an Inhibitor of Lipases from Procine Pancreas and *Pseudomonas*," *Biosci. Biotech. Biochem.* 61(1):102-104 (1997).

Bochenek, W.J. and Rodgers, J.B., "Effect of Polyol Detergents on Cholesterol and Triglyceride Absorption," *Biochimica et Biophysica Acta* 489:503-506 (1977).

Comai, K. and Sullivan, A.C., "Antiobesity activity of pluronic L-101," *International Journal of Obesity* 4:33-42 (1980).

Han, L-K, et al., "Reduction in fat storage during chitin-chitosan treatment in mice fed a high-fat diet," *International Journal of Obesity* 23:174-179 (1999).

Atkinson et al., "Combined Drug Treatment of Obesity," *Obesity Research*, 3(S4):497S-500S (1995).

Sjöström, et al., "Randomised placebo-controlled trial of orlistat for weight loss and prevention of weight regain in obese patients," *The Lancet*, 352:167-172 (1998).

CA Abstract, AN 127:156561, James et al. (1997).

CA Abstract, AN 124:105377, Drent et al. (1995).

* cited by examiner

FAT-BINDING POLYMERS

RELATED APPLICATIONS

This application claims the benefit of U.S. Provisional Application No. 60/302,081, filed Jun. 29, 2001, U.S. Provisional Application No. 60/302,221, filed Jun. 29, 2001, U.S. Provisional Application No. 60/359,473, filed Feb. 22, 2002, U.S. Provisional Application No. 60/359,467, filed Feb. 22, 2002 and U.S. Provisional Application No. 60/359,474, filed Feb. 22, 2002. The entire teachings of these provisional applications are incorporated herein by reference.

BACKGROUND OF THE INVENTION

Human obesity is a recognized health problem with approximately ninety-seven million people considered clinically overweight in the United States. The accumulation or maintenance of body fat bears a direct relationship to caloric intake. Therefore, one of the most common methods for weight control to combat obesity is the use of relatively low-fat diets, that is, diets containing less fat than a "normal diet" or that amount usually consumed by the patient.

The presence of fats in a great many food sources greatly limits the food sources which can be used in a low fat diet. Additionally, fats contribute to the flavor, appearance and physical characteristics of many foodstuffs. As such, the acceptability of low-fat diets and the maintenance of such diets are difficult.

Various chemical approaches have been proposed for controlling obesity. Anorectic agents such as dextroamphetamine, the combination of the non-amphetamine drugs phentermine and fenfluramine (Phen-Fen), and dexfenfluramine (Redux) alone, are associated with serious side effects. Indigestible materials such as olestra (OLEAN®), mineral oil or neopentyl esters (see U.S. Pat. No. 2,962,419) have been proposed as substitutes for dietary fat. Garcinia acid and derivatives thereof have been described as treating obesity by interfering with fatty acid synthesis. Swellable crosslinked vinyl pyridine resins have been described as appetite suppressants via the mechanism of providing non-nutritive bulk, as in U.S. Pat. No. 2,923,662. Surgical techniques such as temporary ileal bypass surgery are employed in extreme cases.

Another chemical approach involves the administration of lipase inhibitors. Lipase inhibitors such as boronate esters are effective in reducing fat uptake, however, they are associated with unpleasant side effects such as steatorrhea. A means of binding the undigested fat in the gastrointestinal tract is needed to remedy side effects associated with lipase inhibitors.

Therefore, methods for treating obesity such as those described above have serious shortcomings with controlled diet remaining the most prevalent technique for controlling obesity. As such, new methods for treating obesity and obesity-related conditions are needed.

SUMMARY OF THE INVENTION

It has now been found that polymers having pendant aminoalkylpolyol, ammoniumalkylpolyol, dialkanolamine, and dialkanolammonium functional groups can bind and sequester fats such as triglyceride esters of saturated and/or unsaturated fatty acids, free fatty acids, diglycerides, monoglycerides, phospholipids, and cholesterol esters in the gastrointestinal tract, preventing side effects of lipase inhibitors. Biological studies described in Example 2 have shown that when rats are fed a diet supplement with 15 weight % lard, rats treated with a lipase inhibitor and a fat-binding polymer of the present invention have less free, unabsorbed fat in their feces than rats treated only with a lipase inhibitor. This class of fat-binding polymers has additionally been found to have minimal side effects and low toxicity when orally administered to animals, including humans. Based on this discovery, novel fat binding polymers, pharmaceutical compositions comprising the same, and methods of removing fat from the gastrointestinal tract of subjects are disclosed herein.

In one embodiment, the present invention is a pharmaceutical composition that comprises a carrier or diluent and a fat binding polymer with one or more aminoalkylpolyol, ammoniumalkylpolyol, dialkanolamine, or dialkanolammonium side chains.

In another embodiment, the present invention is a method for removing fat from the gastrointestinal tract of a subject in need of such treatment. The method comprises the step of administering to the subject an effective amount of one of the fat binding polymers disclosed herein.

In another embodiment, the present invention is a polymer comprising monomer units represented by Structural Formula (I):

where M is a —C(O)—, —NR$_1$—, or —CH$_2$NR$_1$—; Q is a covalent bond or an inert linking group; R$_1$ is —H, an aliphatic group or a substituted aliphatic group; R$_2$ is —H or a C1–C6 alkyl group; and W is an aminoalkylpolyol, an ammoniumalkylpolyol, a dialkanolamine, or a dialkanolammonium.

Polymers of the present invention effectively bind, absorb, or associate with fats, thereby removing fat from the gastrointestinal tract of a subject and preventing side effects, such as steatorrhea, following the administration of a lipase inhibitor. The disclosed polymers have the additional advantage of remaining substantially unabsorbed by the gastrointestinal tract, and therefore have minimal systemic side effects.

DETAILED DESCRIPTION OF THE INVENTION

"Fat-binding polymers" are polymers that absorb, bind or otherwise associate with fat, thereby inhibiting (partially or completely) fat digestion, hydrolysis, or absorption in the gastrointestinal tract and/or facilitate the removal of fat from the body prior to digestion. Fat-binding polymers can also absorb, bind, or otherwise associate with fat that is unabsorbed by the gastrointestinal system. The fat-binding polymers comprise one or more fat-binding regions. "Fat-binding regions" include a positively charged region, and, optionally, a hydrophobic region, or a region that is both positively charged and hydrophobic. The fat-binding region has a positive charge when the region comprises an ionic group such as a quaternary amine or an atom, for example, the nitrogen of an amine that possesses a positive charge under conditions present in the gastrointestinal tract.

"Fats," as that term is used herein, are solid or liquid oils generally consisting of glycerol esters of fatty acids. Sources of fats include both animal and vegetable fats, for example, triglyceride esters of saturated and/or unsaturated fatty acids, free fatty acids, diglycerides, monoglycerides, phospholipids, and cholesterol esters.

Preferred fat binding polymers for use in the disclosed pharmaceutical compositions and methods comprise monomer units represented by Structural Formula (I):

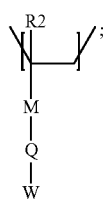

(I)

where M is a covalent bond, —(CH$_2$)$_n$—, 1,3-phenylene, 1,4-phenylene, —C(O)O—, —C(O)NR$_1$—, —C(O)—, —O—, —NR$_1$—, —N$^+$(R$_1$)(R$_3$)—, —CH$_2$NR$_1$—, —CH$_2$N$^+$(R$_1$)(R$_3$)—, or —CH$_2$O—; n is an integer greater than 1; Q is a covalent bond or an inert linking group; R$_1$ is —H, an aliphatic group or a substituted aliphatic group; R$_2$ is —H or a C1–C6 alkyl group, preferably —H or —CH$_3$; R$_3$ is —H, a C1–C6 alkyl group, or a benzyl group, preferably —H or —CH$_3$; W is an aminoalkylpolyol (—NR$_4$R$_5$), dialkanolamine (—N(R$_6$)$_2$), an ammoniumalkylpolyol (—N$^+$(R$_4$)$_2$(R$_5$)), or a dialkanolammonium (—N$^+$(R$_4$)(R$_6$)$_2$); R$_4$ is, independently, —H, alkyl, or benzyl; R$_5$ is a polyol; and R$_6$ is, independently, an alkyl alcohol, also referred to as "alkanol". Preferably, M is a covalent bond, —(CH$_2$)$_n$—, 1,3-phenylene, 1,4-phenylene, —C(O)O—, —C(O)NR$_1$—, —C(O)—, —O—, —NR$_1$—, —CH$_2$NR$_1$—, or —CH$_2$O—; and W is an aminoalkylpolyol or a dialkanolamine. More preferably, M is a 1,3-phenylene, 1,4-phenylene, —C(O)O—, —C(O)NR$_1$—, —C(O)—, —O—, —NR$_1$—, —CH$_2$NR$_1$— or —CH$_2$O—; Q is a covalent bond or an inert linking group; R$_1$ is —H, an aliphatic group or a substituted aliphatic group; R$_2$ is —H or a C1–C6 alkyl group; W is an aminoalkylpolyol or a dialkanolamine; and the remainder of the variables are as defined above. Even more preferably, W is diethanolamine, Q is a C1 to C4 alkylene group, and the remainder of the variables are as defined above.

Particularly preferred fat binding polymers for use in the disclosed pharmaceutical compositions and methods comprise monomer units represented by Structural Formula (II):

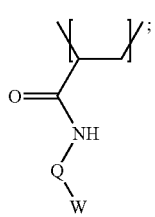

(II)

where Q is a covalent bond or an inert linking group; W is an aminoalkylpolyol, dialkanolamine, an ammoniumalkylpolyol, or a dialkanolammonium; R$_4$ is, independently, —H, alkyl, or benzyl; R$_5$ is a polyol; and R$_6$ is, independently, an alkanol. In a preferred embodiment, W is an aminoalkyl-1,2-diol and Q is a C2 to C4 alkylene group. In an especially preferable embodiment, W is diethanolamine and Q is propylene.

In another embodiment, the present invention is a polyalkyleneimine in which some or all of the nitrogen atoms have one (or two) alkanol group or alkylpolyol groups (preferably dialkanol group). Also include is a pharmaceutical composition comprising a pharmaceutically acceptable carrier or diluent and the polyaklyleneimine and use of the same for one or more of the therapeutic indications described herein. A "polyalkyleneimine" is a polymer in which the backbone comprises nitrogen atoms separated by alkylene groups (e.g., ethylene, propylene, butylene and the like). The alkylene groups in the polymer backbone can be the same or different. Some or all of the nitrogen atoms in the backbone are attached to one (or two) alkanol group or polyol group such as 2-hydroxyethyl or 2,3dihydroxypropyl. One example of a polyalkyleneimine of this type is poly{N-(2-hydroxy)ethyl ethylenimine).

In another embodiment, the present invention is a polymer with monomer units represented by Structural Formula (III) and a pharmaceutical composition comprising a pharmaceutically acceptable carrier or diluent and a polymer with monomer units represented by Structural Formula (III):

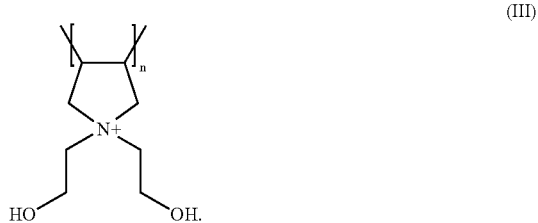

(III)

A subject in need of fat removal from the gastrointestinal tract is a subject with inadequate or deficient lipase activity or another condition which prevents uptake of fat from the gastrointestinal tract. Inadequate or deficient lipase activity can be due, for example, to inadequate lipase production, inactive or partially inactive enzyme, or inhibited enzyme. Typically, a subject in need of fat removal from the gastrointestinal tract is suffering from steatorrhea, which can be caused, for example, by inadequate lipase activity in the subject. Alternatively, a subject in need of fat removal from the gastrointestinal tract can is a subject who is being treated with a lipase inhibitor for one or more of the following conditions: obesity, Type II (non-insulin-dependent) diabetes mellitus, impaired glucose tolerance, hypertension, coronary thrombosis, stroke, lipid syndromes, hyperglycemia, hypertriglyceridemia, hyperlipidemia, sleep apnea, hiatal hernia, reflux esophagisitis, osteoarthritis, gout, cancers associated with weight gain, gallstones, kidney stones, pulmonary hypertension, infertility, cardiovascular disease, above normal weight, and above normal lipid levels; or where the subject would benefit from reduced platelet adhesiveness, weight loss after pregnancy, lowered lipid levels, lowered uric acid levels, or lowered oxalate levels. Often, a subject in need of fat removal from the gastrointestinal tract is obese.

Advantageously, a lipase inhibitor is co-administered to the subject in combination with the fat binding polymer to treat the above conditions. Lipase inhibitors may either be administered separately from the polymer or administered attached to the fat-binding polymer. In one aspect, the lipase inhibitor is hydrolyzed into its unbound, active state in the gastrointestinal tract. Examples include aryl boronate lipase inhibitors attached to a fat-binding polymer, as described in co-pending Provisional U.S. Application having Ser. No. 60/302,221, which is incorporated herein by reference. Alternatively, the lipase inhibitor is covalently attached to the polymer and is active without further modification, as described in U.S. Pat. No. 6,267,952, which is incorporated herein by reference. Suitable lipase inhibitors to be administered separately are described in U.S. Pat. No. 6,264,937, which is incorporated herein by reference, and include lipstatin, tetrahydrolipstatin, and the panclicins.

For Structural Formulae (I) and (II), suitable polymers have side chains where Q is an inert linker group. An inert linking group serves to separate an aminoalkylpolyol, an ammoniumalkylpolyol, a dialkanolamine, or a dialkanolammonium from the polymer backbone. A linking group is "inert" when it contains no functionality that substantially interferes with the fat-binding ability of the polymer. Inert linking groups are preferably substituted or unsubstituted hydrocarbyl groups, optionally containing one or more heteroatoms, such as N, O, and S, and are preferably alkylene groups, preferably C1–C30, more preferably C1 to C15 and even more preferably C1–C8. Typically, inert linking groups are hydrophobic.

Suitable aminoalkylpolyols have an amine nitrogen substituted with at least one alkyl group having two or more hydroxyl substituents. For example, an aminoalkylpolyol can be represented by $-NR_4R_5$, where $R_4$ is $-H$, alkyl, or benzyl, and $R_5$ is a polyol. A polyol is an alkyl group substituted with two or more hydroxyl groups. Preferably, an aminoalkylpolyol is an aminoalkyldiol, more preferably an aminoalkyl-1,2-diol, and even more preferably an aminopropane-1,2-diol. Examples of aminoalkyldiols include 3-aminopropane-1,2-diol, 4-aminobutane-1,2-diol, 4-aminobutane-1,3-diol, 5-aminopentane-1,2-diol, 5-aminopentane-1,3-diol, and 5-aminopentane-1,4-diol.

Dialkanolamines have nitrogen atoms substituted with two alkyl groups, with each alkyl group having one hydroxyl substituent. A dialkanolamine can be represented by $-N(R_6)_2$, where each $R_6$ is independently an alkyl alcohol. Preferred dialkanolamines include diethanolamine, dimethanolamine, dipropanolamine, dibutanolamine, and dipentanolamine.

Ammoniumalkylpolyols have an amine nitrogen substituted with an alkylpolyol and two other groups. For example, an ammoniumalkylpolyol can be represented by $-N^+(R_4)_2R_5$, where $R_4$ is $-H$, alkyl, or benzyl, and $R_5$ is a polyol. Preferably, $R_5$ is a diol. Suitable ammoniumalkyldiols include $-N^+(CH_3)_2CHOHCH_2OH$, $-N^+(H)(CH_3)CHOHCH_2OH$, $-N^+(CH_3)_2CH_2CHOHCH_2OH$, $-N^+(H)(CH_3)CH_2CHOHCH_2OH$, $-N^+(CH_3)_2(CH_2)_2CHOHCH_2OH$, and $-N^+(H)(CH_3)(CH_2)_2CHOHCH_2OH$.

Dialkanolammoniums have nitrogen substituted with two alkanols and one other group. For example, a dialkanolammonium can represented by $-NR_4(R_6)_2$; where $R_4$ is $-H$, alkyl, or benzyl; and each $R_6$ is independently an alkyl alcohol. Suitable dialkanolammoniums include $-N^+(H)(CH_2OH)_2$, $-N^+(H)(CH_2CH_2OH)_2$, $-N^+(H)(CH_2CH_2CH_2OH)_2$, $-N^+(H)(CH_2CH_2CH_2CH_2OH)_2$, $-N^+(H)(CH_2CH_2CH_2CH_2CH_2OH)_2$, $-N^+(CH_3)(CH_2OH)_2$, $-N^+(CH_3)(CH_2CH_2OH)_2$, $-N^+(CH_3)(CH_2CH_2CH_2OH)_2$, $-N^+(CH_3)(CH_2CH_2CH_2CH_2OH)_2$, and $-N^+(CH_3)(CH_2CH_2CH_2CH_2CH_2OH)_2$.

Suitable combinations of Q and W in a monomer unit represented by Structural Formulae (I) or (II) include units where Q is a C1 to C15 alkylene group and W is an aminoalkyldiol, Q is a C1 to C15 alkylene group and W is an aminoalkyl-1,2-diol, Q is a C1 to C15 alkylene group and W is aminopropane-1,2-diol, Q is a C1 to C15 alkylene group and W is diethanolamine, and Q is a C1 to C4 alkylene group and W is diethanolamine. In another preferred embodiment, W is an aminoalkyl-1,2-diol and Q is a C2 to C4 alkylene group.

Preferred combinations of Q and W in a monomer unit represented by Structural Formulae (I) and (II) include units where W is diethanolamine and Q is methylene, ethylene, propylene, or butylene.

Other specific combinations of Q and W include, for example, $-CH_2N(CH_3)CHOHCH_2OH$, $-CH_2N(H)CHOHCH_2OH$, $-CH_2N(CH_3)CH_2CHOHCH_2OH$, $-CH_2N(H)CH_2CHOHCH_2OH$, $-CH_2N(CH_3)(CH_2)_2CHOHCH_2OH$, $-CH_2N(H)(CH_2)_2CHOHCH_2OH$, $-CH_2CH_2N(CH_3)CHOHCH_2OH$, $-CH_2CH_2N(H)CHOHCH_2OH$, $-CH_2CH_2N(CH_3)CH_2CHOHCH_2OH$, $-CH_2CH_2N(H)CH_2CHOHCH_2OH$, $-CH_2CH_2N(CH_3)(CH_2)_2CHOHCH_2OH$, $-CH_2CH_2N(H)(CH_2)_2CHOHCH_2OH$, $-CH_2CH_2CH_2N(CH_3)CHOHCH_2OH$, $-CH_2CH_2CH_2N(H)CHOHCH_2OH$, $-CH_2CH_2CH_2N(CH_3)CH_2CHOHCH_2OH$, $-CH_2CH_2CH_2N(H)CH_2CHOHCH_2OH$, $-CH_2CH_2CH_2N(CH_3)(CH_2)_2CHOHCH_2OH$, $-CH_2CH_2CH_2N(H)(CH_2)_2CHOHCH_2OH$, $-CH_2N(CH_2OH)_2$, $-CH_2N(CH_2CH_2OH)_2$, $-CH_2N(CH_2CH_2CH_2OH)_2$, $-CH_2N(CH_2CH_2CH_2CH_2OH)_2$, $-CH_2N(CH_2CH_2CH_2CH_2CH_2OH)_2$, $-CH_2CH_2N(CH_2OH)_2$, $-CH_2CH_2N(CH_2CH_2OH)_2$, $-CH_2CH_2N(CH_2CH_2CH_2OH)_2$, $-CH_2CH_2N+(CH_2CH_2CH_2CH_2OH)_2$, $-CH_2CH_2N(CH_2CH_2CH_2CH_2CH_2OH)_2$, $-CH_2CH_2CH_2N(CH_2OH)_2$, $-CH_2CH_2CH_2N(CH_2CH_2OH)_2$, $-CH_2CH_2CH_2N(CH_2CH_2CH_2OH)_2$, $-CH_2CH_2CH_2N(CH_2CH_2CH_2CH_2OH)_2$, $-CH_2CH_2CH_2N(CH_2CH_2CH_2CH_2CH_2OH)_2$, $-CH_2N^+(CH_3)_2CHOHCH_2OH$, $-CH_2N^+(H)(CH_3)CHOHCH_2OH$, $-CH_2N^+(CH_3)_2CH_2CHOHCH_2OH$, $-CH_2N^+(H)(CH_3)CH_2CHOHCH_2OH$, $-CH_2N^+(CH_3)_2(CH_2)_2CHOHCH_2OH$, $-CH_2N^+(H)(CH_3)(CH_2)_2CHOHCH_2OH$, $-CH_2CH_2N^+(CH_3)_2CHOHCH_2OH$, $-CH_2CH_2N^+(H)(CH_3)CHOOHCH_2OH$, $-CH_2CH_2N^+(CH_3)_2CH_2CHOHCH_2OH$, $-CH_2CH_2N^+(H)(CH_3)CH_2CHOHCH_2OH$, $-CH_2CH_2N^+(CH_3)_2(CH_2)_2CHOHCH_2OH$, $-CH_2CH_2N^+(H)(CH_3)(CH_2)_2CHOHCH_2OH$, $-CH_2CH_2CH_2N^+(CH_3)_2CHOHCH_2OH$, $-CH_2CH_2CH_2N^+(H)(CH_3)CHOHCH_2OH$, $-CH_2CH_2CH_2N^+(CH_3)_2CH_2CHOHCH_2OH$, $-CH_2CH_2CH_2N^+(H)(CH_3)CH_2CHOHCH_2OH$, $-CH_2CH_2CH_2N^+(CH_3)_2(CH_2)_2CHOHCH_2OH$, $-CH_2CH_2CH_2N^+(H)(CH_3)(CH_2)_2CHOHCH_2OH$, $-CH_2N^+(H)(CH_2OH)_2$, $-CH_2N^+(H)(CH_2CH_2OH)_2$, $-CH_2N^+(H)(CH_2CH_2CH_2OH)_2$, $-CH_2N^+(H)(CH_2CH_2CH_2CH_2OH)_2$, $-CH_2N^+(H)(CH_2CH_2CH_2CH_2CH_2OH)_2$, $-CH_2N^+(CH_3)(CH_2OH)_2$, $-CH_2N^+(CH_3)(CH_2CH_2OH)_2$, $-CH_2N^+(CH_3)(CH_2CH_2CH_2OH)$, $-CH_2N^+(CH_3)(CH_2CH_2CH_2CH_2OH)$, $-CH_2N^+(CH_3)(CH_2CH_2CH_2CH_2CH_2OH)$, $-CH_2CH_2N^+(H)(CH_2OH)_2$, $-CH_2CH_2N^+(H)(CH_2CH_2OH)_2$, —CH₂CH₂N⁺(H)(CH₂CH₂CH₂OH)₂, —CH₂CH₂N⁺(H)(CH₂CH₂CH₂CH₂OH)₂, —CH₂CH₂N⁺(H)(CH₂CH₂CH₂CH₂CH₂OH)₂, —CH₂CH₂N⁺(CH₃)(CH₂OH)₂, —CH₂CH₂N⁺(CH₃)(CH₂CH₂OH)₂, —CH₂CH₂N⁺(CH₃)(CH₂CH₂CH₂OH)₂, —CH₂CH₂N⁺(CH₃)(CH₂CH₂CH₂CH₂OH)₂, —CH₂CH₂N⁺(CH₃)(CH₂CH₂CH₂CH₂CH₂OH)₂, —CH₂CH₂CH₂N⁺(H)(CH₂OH)₂, —CH₂CH₂CH₂N⁺(H)(CH₂CH₂OH)₂, —CH₂CH₂CH₂N⁺(H)(CH₂CH₂CH₂OH)₂, —CH₂CH₂CH₂N⁺(H)(CH₂CH₂CH₂CH₂OH)₂, —CH₂CH₂CH₂N⁺(H)(CH₂CH₂CH₂CH₂CH₂OH)₂, —CH₂CH₂CH₂N⁺(CH₃)(CH₂OH)₂, —CH₂CH₂CH₂N⁺(CH₃)(CH₂CH₂OH)₂, —CH₂CH₂CH₂N⁺(CH₃)(CH₂CH₂CH₂OH)₂, —CH₂CH₂CH₂N⁺(CH₃)(CH₂CH₂CH₂CH₂OH)₂, and —CH₂CH₂CH₂N⁺(CH₃)(CH₂CH₂CH₂CH₂CH₂OH)₂.

Suitable examples of combinations of M, Q, and W include, for example, —CH₂NH(CH₂)₁CHOHCH₂ OH, —CH₂NH(CH₂)₂CHOHCH₂OH, —CH₂NH(CH₂)₃ CHOHCH₂OH, —CH₂CH₂NH(CH₂)₁CHOHCH₂OH, —CH₂CH₂NH(CH₂)₂CHOHCH₂OH, —CH₂CH₂NH—(CH₂)₃CHOHCH₂OH, -(1,4-phenylene)CH₂NH(CH₂)₁ CHOHCH₂OH, -(1,4-phenylene)CH₂NH(CH₂)₂ CHOHCH₂OH, -(1,4-phenylene)CH₂NH(CH₂)₃ CHOHCH₂OH, -(1,4-phenylene)NH(CH₂)₁ CHOHCH₂OH, -(1,4-phenylene)NH(CH₂)₂ CHOHCH₂OH, -(1,4-phenylene)NH(CH₂)₃ CHOHCH₂OH, —C(O)OCH₂CH₂CH₂N(CH₂CH₂OH)₂, and —C(O)OCH₂CH₂N(CH₂CH₂OH)₂.

Suitable combination of R₂, M, Q, and W include combinations of any of the values of M, Q, and W listed above, where R₂ is —H or methyl. Specific examples include combinations where R₂ is —H or methyl, M is —C(O)O— or —C(O)NH—, Q is ethylene or propylene, and W is diethanolamine. Other combinations include combinations where R₂ is —H or methyl, M is —C(O)O— or —C(O)NH—, and -QW is any one of the combinations described above. Yet other combinations include combinations where R₂ is —H, M is —C(O)O— or —C(O)NH—, Q is ethylene or propylene, and W is diethanolamine.

A phenylene is a phenyl group that forms bonds with two other carbons. Phenylenes are numbered to indicate where on the phenyl ring the carbons are attached. Phenylene can be substituted or unsubstituted.

A hydrocarbyl group is a saturated or unsaturated carbon chain, which typically includes about 1 to about 30 carbon atoms, preferably about 1 to about 15 carbon atoms, and more preferably about 1 to about 8 carbon atoms. A hydrocarbyl group may be interrupted by one or more heteroatoms, such as nitrogen, oxygen, and sulfur. Preferred hydrocarbyl groups are alkyl or aliphatic groups.

An "aliphatic group" is non-aromatic, consists solely of carbon and hydrogen and may optionally contain one or more units of unsaturation, e.g., double and/or triple bonds. An aliphatic group may be straight chained or branched and typically contains between about 1 and about 24 carbon atoms, more typically between about 1 and about 12 carbon atoms.

Aliphatic groups are preferably lower alkyl groups or lower alkylene groups, which include C1–24 (preferably C1–C12) straight chained or branched saturated hydrocarbons. An alkyl group is a saturated hydrocarbon in a molecule that is bonded to one other group in the molecule through a single covalent bond from one of its carbon atoms. Examples of lower alkyl groups include methyl, ethyl, n-propyl, iso-propyl, n-butyl, sec-butyl and tert-butyl. An alkylene group is a saturated hydrocarbon in a molecule that is bonded to two other groups in the molecule through single covalent bonds from two of its carbon atoms. Examples of lower alkylene groups include methylene, ethylene, propylene, iso-propylene (—CH(CH₂)CH₂—), butylene, sec-butylene (—CH(CH₃)CH₂CH₂—), and tert-butylene (—C(CH₃)₂CH₂—).

Suitable substituents for aliphatic, alkyl, phenylene, and hydrocarbyl groups are those which do not significantly lower the fat-binding ability of the polymer, for example, do not lower the fat-binding activity by more than a factor of about two. Examples include —OH, halogen (—Br, —Cl, —I and —F), —O(R'), —O—CO—(R'), —CN, —NO₂, —COOH, =O, —NH₂, —NH(R'), —N(R')₂, —COO(R'), —CONH₂, —CONH(R'), —CON(R')₂, —SH and —S(R'). Each R' is independently an alkyl group or an aryl group. A substituted aliphatic group can have more than one substituent.

Also included in the present invention are pharmaceutically acceptable salts of the disclosed polymers. For example, polymers that have acid functional groups can also be present in the anionic, or conjugate base, form, in combination with a cation. Suitable cations include alkaline earth metal ions, such as sodium and potassium ions, alkaline earth ions, such as calcium and magnesium ions, and unsubstituted and substituted (primary, secondary, tertiary and quaternary) ammonium ions. Polymers that have basic groups such as amines can also be protonated with a pharmaceutically acceptable counter anion, such as chloride, bromide, acetate, formate, citrate, ascorbate, sulfate or phosphate. Similarly, ammonium groups comprise a pharmaceutically acceptable counteranion.

Pharmaceutical compositions of the present invention can include a homopolymer or a copolymer comprising monomer units represented by Structural Formulae (I) and/or (II). A copolymer can include a hydrophilic comonomer. A copolymer can also be a terpolymer, which can include a neutral, hydrophilic comonomer and a hydrophobic comonomer.

In one aspect, the polymer comprises monomers having both cationic and hydrophobic groups. For example, fat-binding polymers of this type can be a homopolymer, copolymer or terpolymer comprising a dialkanolamine, a dialkanolammonium, an aminoalkylpolyol, or an ammoniumalkylpolyol in the polymer side chains, provided that the side chain comprises a hydrophobic group (e.g., where M is a hydrophobic group). A "hydrophobic group" is an alkylene that is more soluble in octanol than in water, or that is insoluble in water. The dialkanolamine or aminoalkylpolyol comprises an amine, which can be protonated in vivo to form a cationic group. Alternatively, a dialkanolammonium group or an alkylammoniumpolyol is present in place of the dialkanolamine or aminoalkylpolyol. Another example of a fat-binding polymer of this type is a copolymer or terpolymer comprising a monomer with a pendant aminoalkylpolyol, ammoniumalkylpolyol, dialkanolamine, or dialkanolammonium, and a monomer having both cationic and hydrophobic groups.

In another aspect, the fat-binding polymer includes monomers having a pendant aminoalkylpolyol, ammoniumalkylpolyol, dialkanolamine, or dialkanolammonium together with a combination of separate monomers each having either a cationic or a hydrophobic functional group. Examples of monomers having a cationic group and monomers having hydrophobic groups are provided below.

In another aspect, the fat-binding polymer comprises monomers having both cationic and neutral functional groups (e.g., a hydroxy group or a carboxamide group).

Fat-binding polymers of this type include homopolymers, copolymers or terpolymers having a monomer with an aminoalkylpolyol, an ammoniumalkylpolyol, a dialkanolamine, or a dialkanolammonium in the polymer side chains. The aminoalkylpolyol and dialkanolamine have an amine which can be protonated in vivo. Alternatively, the fat-binding polymer of this type is a co-polymer or terpolymer including a monomer with a pendant aminoalkylpolyol, ammoniumalkylpolyol, dialkanolamine, or dialkanolammonium and a monomer having both a neutral and a cationic functional group. Examples of monomers having both a neutral and a cationic functional group include aliphatic amine monomers wherein the amine group is derivatized with a hydroxy alkyl group (e.g., N-ω-hydroxyalkyl)allylamine and N-(ω-hydroxyalkyl)vinylamine).

Alternatively, the fat-binding polymer comprises a combination of separate monomers each having either a cationic or a neutral functional group. Fat-binding polymers of this type include copolymers having a monomer with a pendant aminoalkylpolyol, ammoniumalkylpolyol, dialkanolamine, or dialkanolammonium and a cationic monomer such an aliphatic amine monomer. In another example, the fat-binding polymer is a terpolymer comprising a monomer with a pendant aminoalkylpolyol, ammoniumalkylpolyol, dialkanolamine, or dialkanolammonium, a cationic monomer (e.g., an aliphatic amine monomer) and a neutral co-monomer (e.g., vinyl alcohol, allyl alcohol and acrylamide).

Cationic monomers include monomers which contain amine groups, i.e., "amine monomers". Specific examples of aliphatic amine monomers include allylamine, diallylamine, diallylmethylamine and vinylamine. Other amine monomers include aminostyrene, vinylimidazolyl, vinylpyridinyl, dimethylaminomethylstyrene, and diallylmethylammonium chloride. Yet other examples of amine monomers include amine or quaternary amine-containing moieties used in conjunction with acrylate or acrylamide polymers. Examples include aminoalkyl esters or ammoniumalkyl (e.g., trialkylammonium alkyl) esters of an acrylate monomer (e.g., trimethylammonium ethyl methacrylate and trimethylammonium ethyl acrylate) or N-aminoalkyl amide or N-ammoniumalkyl amides (e.g., N-trialkylammonium alkyl) of acrylamides (e.g., N-trimethylammonium ethyl methacryamide and N-trimethylammonium ethyl acrylamide).

As noted above, an amine monomer can comprise one or more hydrophobic regions which are bound to the amine nitrogen of the amine monomer to form a monomer with both a cationic and hydrophobic group. Examples include N-(C4–C30)alkylvinylamine, N-(C4–C30)alkylallylamine, N-(C4–C30)alkyldiallylamine, N-(C4–C30)alkylaminostyrene and N,N-(C1–C30)dialkylaminostyrene.

Hydrophobic monomers are monomers which lack a cationic group and comprise a hydrophobic group. Examples include styrene, (C6–C30) olefinic monomers (e.g., hexene, heptene, octene), (C4–C30)alkylacrylates, (C4–C30)alkylmethacrylates, N-(C4–C30)alkylacrylamides, N-(C4–C30)alkylmethacrylamides, styrene (e.g., fluorstyrene and pentaflourostyrene), vinylnaphthalene, ethylvinylbenzene, vinylbiphenyl, and vinylanisole.

Neutral, hydrophilic monomers are monomers that lack charged groups and comprise a hydrophilic group. Examples include hydroxyethylacrylate, methacrylamide, acrylamide and methacrylamide.

A "subject" is preferably a mammal, such as a human, but can also be a companion animal (e.g., dog, cat, and the like), farm animal (e.g., cow, sheep, pig, horse, and the like) or laboratory animal (e.g., rat, mouse, guinea pig, and the like) in need of treatment for obesity.

The polymers of the present invention are suitable as a medicament for binding fat. As such, they are administered in a manner suitable for reaching the gastrointestinal tract during digestion. They are therefore preferably administered orally as soon as up to about one hour prior to a meal and as late as to up to about one hour subsequent to a meal. Preferably, the polymer is of sufficiently high molecular weight to resist absorption, partially or completely, from the gastrointestinal tract into other parts of the body. The polymers can have molecular weights ranging from about 500 Daltons to about 500,000 Daltons, preferably from about 2,000 Daltons to about 150,000 Daltons.

An "effective amount" is the quantity of polymer that reduces, inhibits, or prevents side effects of a co-administered lipase inhibitor or the symptoms of steatorrhea. Typical dosages range from about 5 milligrams/day to about 10 grams/day, preferably from about 50 milligrams/day to about 5 grams/day. The polymer can be administered alone or in a pharmaceutical composition comprising the polymer, an acceptable carrier or diluent and, optionally, one or more additional drugs, typically one or more additional drugs used for weight reduction (e.g., XENICAL or MERIDIA). Typically, the pharmaceutical composition comprises an effective concentration of the polymer, which has a concentration that can administer an effective amount of the polymer.

The precise amount of polymer being administered to a subject will be determined on an individual basis and will depend on, at least in part, the subject's individual characteristics, such as general health, age, sex, body weight and tolerance to drugs, the degree to which the subject is overweight and the amount of weight reduction sought, the amount of lipase inhibitor administered to the subject, and the amount of fat being consumed and/or excreted.

The disclosed polymers can be administered to the subjects in conjunction with an acceptable pharmaceutical carrier or diluent as part of a pharmaceutical composition for removal of fat from the gastrointestinal tract. Formulations vary according to the route of administration selected, but for oral administration are typically capsules. Solutions and emulsions are also possible.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Typically, the fat binding polymer of the present invention excludes poly(N,N-diallyl-N,N-di(2,3-dihydroxylpropyl) amines and salts thereof such as poly(N,N-diallyl-N,N-di(2, 3-dihydroxylpropyl)ammonium chloride), poly(N,N-diallyl-N-alkyl-N-(2,3-dihydroxylpropyl)amines and salts thereof such as poly(N,N-diallyl-N-alkyl-N-(2,3-dihydroxylpropyl)ammonium chloride), and/or poly(N,N-di(2,3-dihydroxypropyl)allylamine)s and salts thereof such as poly(N, N-di(2,3-dihydroxypropyl)allylamine) hydrochloride. In other instances, poly(N,N-diallyl-N,N-alkyl)amines and salts thereof where at least one of the alkyl group is a 1,2-diol and/or poly(N,N-dialkylallylamine)s and salts thereof where the alkyl groups are 1,2-diols are excluded. Poly(N,N-diallyl-N,N-dialkyl)amines and salts thereof where at least one of the alkyl groups is a diol and/or poly(N,N-dialkylallylamines) and salts thereof where the alkyl groups are diols can also be excluded. In some embodiments, polyallylamines and/or polydiallylamines are excluded. In other embodiments, polyolefins with an aliphatic side chain are excluded.

In some aspects, the polyalkyleneimines described herein exclude poly{N-(2-hydroxy)ethyl ethylenimine).

The fat-binding polymers of the present invention may be prepared by polymerization of a dialkanolamine-, dialkanolammonium-, ammoniumalkylpolyol-, or aminoalkylpolyol-functionalized monomer. This can be accomplished via standard methods of free radical, cationic or anionic polymerization which are well known in the art. Due to reactivity differences between two monomers, the composition of a copolymer produced in this way can differ from the composition of the starting mixture. This reactivity difference can also result in a non-random distribution of monomers along the polymer chain.

The invention is further illustrated by the following examples which are not intended to be limiting in any way.

EXEMPLIFICATION

EXAMPLE 1

Synthesis of Poly(N-Diethanolaminopropyl)Acrylamide

Step 1: Synthesis of (N-Diethanolaminopropyl)Acrylamide

A 2-liter, 3-necked, round-bottomed flask with overhead stirring was charged with 80.08 grams of N-(3-aminopropyl) diethanolamine and 200 milliliters of deionized water. To this mixture was added 3.18 grams of $K_2CO_3$ and the resulting solution was cooled to less than 5° C. with an ice bath. One hundred thirty milliliters of dichloromethane was added with vigorous stirring. This was followed by the addition of 45.0 milliliters of acryloylchloride in 50 milliliters of dichloromethane.

A 50% aqueous solution of KOH was prepared by dissolving 20.58 grams of KOH in 25 milliliters of deionized water. About half of the acryloylchloride solution was added over 30 to 45 minutes until the pH was between 7 and 8. The KOH solution and the acryloylchloride solution were then added dropwise simultaneously, keeping the pH between 8 and 9. The reaction was stirred overnight and allowed to warm to room temperature. The next day, the aqueous layer was separated from the organic layer, which was discarded.

The water was removed at 30° C. to 35° C. using a rotary evaporator until orange/brown oil remained. The KCl was filtered during this procedure. The oil was then dissolved in 500 milliliters of methanol and stirred for 20 minutes. The remaining KCl was then filtered. The methanol then removed in vacuo, leaving orange/brown oil. This monomer (126.7 grams) is used directly for polymerization without further purification.

Step 2: Synthesis of Poly(N-Diethanolaminopropyl)Acrylamide 126.7 grams of (N-diethanolaminopropyl)acrylamide was dissolved in 750 milliliters of deionized water (about 15% w/v) in a 1-liter, round-bottomed flask. To this solution was added 0.4942 grams (about 0.5 wt %) of V-50 initiator as a solid. The vessel was purged with nitrogen for 30 minutes to obtain a clear, golden-colored and homogeneous solution. The mixture was heated at 65° C. After about 18 hours of heating, a second batch of V50 (0.2761 grams dissolved in 3.0 milliliters of deionized water) was added to the reaction. After about 42 hours of heating, a third batch of V50 (0.2644 grams dissolved in 3.0 milliliters of deionized water) was added. After another 72 hours, the heat was removed and the reaction mixture was allowed to cool to room temperature.

The material was dialyzed (molecular weight cut off 3.5 K) over 24 hours with a water change after 16 hours. The purified polymer was then dried in a forced air oven at 50° C. for 30 hours. An orange and tacky film was obtained and was then redissolved in 300 milliliters of methanol. The solvent was removed in vacuo to yield an oil, which was then precipitated into 3 liters of ether. The gummy mass was then vacuum dried at about 35° C. to 40° C. for 16 hours. The final yield of was 50 grams of a grindable, yellow solid.

EXAMPLE 2

Poly(N-Diethanolaminopropylacrylamide) Reduces Free, Unabsorbed Fat in Rat Feces The model consists of male, Sprague Dawley rats obtained from Taconic Farms, 200 g, housed individually in wire mesh cages. They were acclimated to the facility for six days, during which time they were fed a chow based diet supplemented with 15 percent lard by weight. Feed and water were provided ad libitum. The animals were then randomly assigned to groups of five and fed test diets for three days. The test diet was also a chow based feed. A lipase inhibitor (Orlistat) was added at 0.04 percent by weight and poly(N-diethanolaminopropyl)acrylamide was added at 0.10–0.50 percent by weight. Orlistat was mixed in the feed as a powder, while the polymer was first dissolved in 20 mL water and then mixed in the feed, followed by the addition of the supplemented fat in the form of lard at 15 percent by weight. During the final 24 hours of the treatment period an 8.5"×11" sheet of white paper was placed beneath each cage.

One inch squares were drawn on the paper creating a grid of 80 squares. When oil in the form of unabsorbed dietary triglyceride seeped from the stool, it stained the paper. This was readily discerned from urine if the papers were allowed to dry for six hours. The oil stains conferred translucence to the paper. The squares that contained these oil stains were counted and expressed as a percentage of total area stained.

The following results were obtained:

| Group # | Weight % poly(N-diethanolamino-propylacrylamide) | % Area Stained | % of Feed Consumed That Was Excreted | Food Consumption-% of Control |
|---|---|---|---|---|
| 1 | 0.0 | 41 | 53 | 100 |
| 2 | 0.1 | 30 | 33 | 109 |
| 3 | 0.2 | 12 | 32 | 111 |
| 4 | 0.3 | 9 | 36 | 108 |
| 5 | 0.5 | 5 | 44 | 98 |

The results demonstrated that poly(N-diethanolaminopropylacrylamide) reduces free, unabsorbed fat in rat feces in a dose-dependent manner. Therefore, the fat-binding polymers of the present invention are effective in reducing the amount of free, unabsorbed fat in the feces of subjects, particularly those receiving a lipase inhibitor.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a polymer with one or more side chains comprising an aminoalkylpolyol, an ammoniumalkylpolyol, a dialkanolamine, a dialkanolammonium, or a pharmaceutically acceptable salt thereof, provided that the polymer is not a polyallylamine or a polydiallylamine.

2. The pharmaceutical composition of claim 1, wherein the polymer is a polymer with monomer units represented by Structural Formula (I):

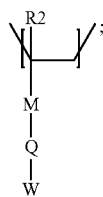

or a pharmaceutically acceptable salt thereof;
wherein:
M is a covalent bond, —$(CH_2)_n$—, 1,3-phenylene, 1,4-phenylene, —C(O)O—, —C(O)$NR_1$, —C(O)—, —O—, —$NR_1$—, —$N^+(R_1)(R_3)$—, —$CH_2NR_1$—, —$CH_2N^+(R_1)(R_3)$, or —$CH_2O$—;

n is an integer greater than 1;
Q is a covalent bond or an inert linking group;
$R_1$ is —H, an aliphatic group or a substituted aliphatic group;
$R_2$ is —H or a C1–C6 alkyl group;
$R_3$ is —, a C1–C6 alkyl group, or a benzyl group;
W is —$NR_4R_5$, —$N(R_6)_2$, —$N^+(R_4)_2R_5$, or —$N^+R_4(R_6)_2$;
each $R_4$ is, independently, —H, alkyl, or benzyl;
$R_5$ is a polyol; and
each $R_6$ is, independently, an alkanol.

3. The pharmaceutical composition of claim 2, wherein M is a covalent bond, —$(CH_2)_n$—, 1,3-phenylene, 1,4-phenylene, —C(O)O—, —C(O)$NR_1$, —C(O)—, —O—, —$NR_1$—, —$CH_2NR_1$—, or —$CH_2O$—; and W is an aminoalkylpolyol or a dialkanolamine.

4. The pharmaceutical composition of claim 1, wherein the polymer is a polymer with monomer units represented by Structural Formula (I):

or a pharmaceutically acceptable salt thereof,
wherein:
M is a 1,3-phenylene, 1,4-phenylene, —C(O)O—, —C(O)$NR_1$, —C(O)—, —O—, —$NR_1$—, —$CH_2NR_1$— or —$CH_2O$—;
Q is a covalent bond or an inert linking group;
$R_1$ is —H, an aliphatic group or a substituted aliphatic group;
$R_2$ is —H or a C1–C6 alkyl group;
W is —$NR_4R_5$, —$N(R_6)_2$, —$N^+(R_4)_2R_5$, or —$N^+R_4(R_6)_2$;
each $R_4$ is, independently, —H, alkyl, or benzyl;
$R_5$ is a polyol; and
each $R_6$ is, independently, an alkanol.

5. The pharmaceutical composition of claim 3 wherein Q is a C1 to C30 alkylene group.

6. The pharmaceutical composition of claim 5 wherein Q is a C1 to C15 alkylene group.

7. The pharmaceutical composition of claim 6 wherein W is diethanolammoniumdiol or an ammoniumalkyldiol.

8. The pharmaceutical composition of claim 5 wherein W is an aminoalkyl-1,2-diol.

9. The pharmaceutical composition of claim 8 wherein W is aminopropane-1,2-diol.

10. The pharmaceutical composition of claim 5 wherein W is diethanolamine.

11. The pharmaceutical composition of claim 4 wherein W is diethanolamine and Q is a C1 to C4 alkylene group.

12. The pharmaceutical composition of claim 4 wherein R2 is —H or methyl, M is C(O)O— or C(O)NH—, Q is ethylene or propylene, and W is diethanolamine.

13. The pharmaceutical composition of claim 1, wherein the polymer is a polymer with monomer units represented by Structural Formula (II):

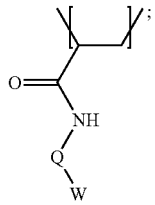

(II)

or a pharmaceutically acceptable salt thereof;
wherein:
Q is a covalent bond or an inert linking group;
W is —$NR_4R_5$, —$N(R_6)_2$, —$N^+(R_4)_2R_5$, or —$N^+R_4(R_6)_2$;
each $R_4$ is, independently, —H, alkyl, or benzyl;
$R_5$ is a polyol; and
each $R_6$ is, independently, an alkanol.

14. The pharmaceutical composition of claim 13 wherein Q is a C1 to C30 alkylene group.

15. The pharmaceutical composition of claim 14 wherein Q is a C1 to C15 alkylene group.

16. The pharmaceutical composition of claim 15 wherein W is an aminoalkyldiol.

17. The pharmaceutical composition of claim 16 wherein W is an aminoalkyl-1,2-diol.

18. The pharmaceutical composition of claim 17 wherein W is an aminoalkyl-1,2-diol and Q is a C2 to C4 alkylene group.

19. The pharmaceutical composition of claim 14 wherein W is diethanolamine.

20. The pharmaceutical composition of claim 14 wherein W is diethanolamine, $N^+H(CH_2OH)_2$, or $N^+(CH_3)(CH_2OH)_2$; and Q is ethylene or propylene.

21. The pharmaceutical composition of claim 13, wherein -Q is ethylene or propylene; and W is diethanolamine.

22. The pharmaceutical composition of claim 2 wherein the polymer is a homopolymer.

23. The pharmaceutical composition of claim 3 wherein the polymer is a copolymer comprising a hydrophobic comonomer.

24. The pharmaceutical composition of claim 23 wherein the copolymer is a terpolymer comprising a neutral, hydrophilic comonomer and a hydrophobic comonomer.

25. A method for removing fat from the gastrointestinal tract of a subject in need of such treatment, said method comprising the step of administering to the subject an effective amount of a polymer with one or more side chains comprising an aminoalkylpolyol, an ammoniumalkylpolyol, a dialkanolamine, a dialkanolammonium, or a pharmaceutically acceptable salt thereof, provided that the polymer is not a polyallylamine or a polydiallylamine.

26. The method of claim 25, wherein the polymer is a polymer with monomer units represented by Structural Formula (II):

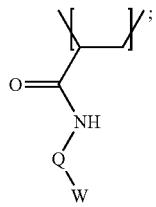

(II)

or a pharmaceutically acceptable salt thereof;
wherein:
Q is a covalent bond or an inert linking group;
W is —$NR_4R_5$, —$N(R_6)_2$, —$N^+(R_4)_2R_5$, or —$N^+R_4(R_6)_2$;
each $R_4$ is, independently, H, alkyl, or benzyl;
$R_5$ is a polyol; and
each $R_6$ is, independently, an alkanol.

27. The method of claim 25, wherein the polymer is a polymer with monomer units represented by Structural Formula (I):

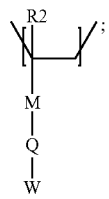

(I)

or a pharmaceutically acceptable salt thereof;
wherein:
M is 1,3-phenylene, 1,4-phenylene, —C(O)O—, —C(O)$NR_1$, —C(O)—, —O—, —$NR_1$—, —$CH_2NR_1$—or —$CH_2O$—;
Q is a covalent bond or an inert linking group;
$R_1$ is —H, an aliphatic group or a substituted aliphatic group;
$R_2$ is —H or a C1–C6 alkyl group; and
W is —$NR_4R_5$, —$N(R_6)_2$, —$N^+(R_4)_2R_5$, or —$N^+R_4(R_6)_2$;
$R_4$ is, independently, —H, alkyl, or benzyl;
$R_5$ is a polyol; and
$R_6$ is, independently, an alkanol.

28. The method of claim 27, wherein the subject is obese.

29. The method of claim 27, wherein the subject is being treated for Type II (non-insulin-dependent) diabetes mellitus.

30. The method of claim 27, wherein the subject is being treated for one or more of the following conditions, selected from:
steatorrhea, impaired glucose tolerance, hypertension, coronary thrombosis, stroke, lipid syndromes, hyperglycemia, hypertriglyceridemia, hyperlipidemia, sleep apnea, hiatal hernia, reflux esophagisitis, osteoarthritis, gout, cancers associated with weight gain, gallstones, kidney stones, pulmonary hypertension, infertility, cardiovascular disease;
or wherein the subject is being treated to reduce platelet adhesiveness, to lower weight loss after pregnancy, lower lipid levels, lower uric acid levels, or lower oxalate levels.

31. The method of claim 27 wherein Q is a C1 to C15 alkylene group and W is an aminoalkyldiol.

32. The method of claim 31 wherein Q is a C1 to C15 alkylene group and W is an aminoalkyl-1,2-diol.

33. The method of claim 27 wherein Q is a C1 to C15 alkylene group and W is diethanolamine.

34. The method of claim 26, wherein -W is an aminoalkylpolyol or a dialkanolamine.

35. The method of claim 34 wherein Q is a C1 to C15 alkylene group and W is an aminoalkyldiol.

36. The method of claim 35 wherein Q is a C1 to C15 alkylene group and W is an aminoalkyl-1,2-diol.

37. The method of claim 34 wherein Q is a C1 to C15 alkylene group and W is diethanolamine.

38. A polymer comprising monomer units represented by Structural Formula (I):

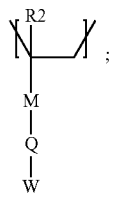

(I)

wherein:
M is a —C(O)—, —NR$_1$—, or —CH$_2$NR$_1$—;
Q is a covalent bond or an inert linking group;
R$_1$ is —H, an aliphatic group or a substituted aliphatic group;
R$_2$ is —H or a C$_1$–C6 alkyl group; and
W is an aminoalkylpolyol or a dialkanolamine.

39. A polymer comprising monomer units represented by Structural Formula (III):

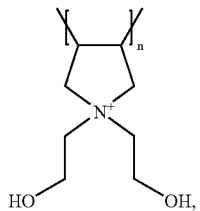

(III)

or a pharmaceutically acceptable salt thereof.

40. The pharmaceutical composition of claim 1, wherein the polymer is a polymer with monomer units represented by Structural Formula (III):

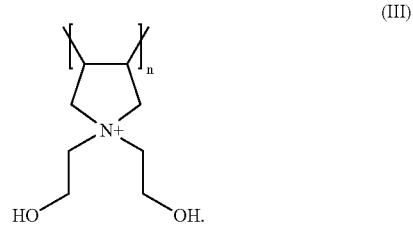

(III)

41. A polymer comprising monomer units represented by Structural Formula (II):

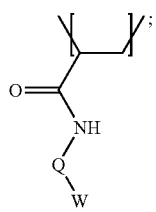

(II)

or a pharmaceutically acceptable salt thereof;
wherein:
Q is a covalent bond or an inert linking group;
W is —NR$_4$R$_5$, —N(R$_6$)$_2$, —N$^+$(R$_4$)$_2$R$_5$, or —N$^+$R$_4$(R$_6$)$_2$;
each R$_4$ is, independently, —H, alkyl, or benzyl;
R$_5$ is a polyol; and
each R$_6$ is, independently, an alkanol.

42. The polymer of claim 41, wherein
Q is ethylene or propylene; and
W is diethanolamine.

* * * * *

UNITED STATES PATENT AND TRADEMARK OFFICE
CERTIFICATE OF CORRECTION

PATENT NO. : 7,049345 B2
APPLICATION NO. : 10/187315
DATED : May 23, 2006
INVENTOR(S) : Stephen Randall Holmes-Farley It is certified that error appears in the above-identified patent and that said Letters Patent is hereby corrected as shown below:

\*\* Column 14, line 6, phrase "$R_3$ is —" should read "$R_3$ is —H"\*\*

Signed and Sealed this

Fifteenth Day of August, 2006

JON W. DUDAS
*Director of the United States Patent and Trademark Office*